United States Patent [19]
Lu et al.

[11] Patent Number: 5,981,757
[45] Date of Patent: Nov. 9, 1999

[54] NIZATIDINE PREPARATION

[75] Inventors: Yee-Fung Lu, Scarborough; James L. A. Tindall, Goodwood, both of Canada

[73] Assignee: Torcan Chemical Ltd., Aurora, Canada

[21] Appl. No.: 09/017,209

[22] Filed: Feb. 2, 1998

[51] Int. Cl.[6] .................................................. C07D 277/30
[52] U.S. Cl. ............................................................ 548/205
[58] Field of Search ............................................. 548/205

[56] References Cited

U.S. PATENT DOCUMENTS

| | | |
|---|---|---|
| 5,541,335 | 7/1996 | Manning . |
| 5,574,054 | 11/1996 | Kitagawa et al. . |
| 5,700,945 | 12/1997 | Manning ................................. 548/203 |

FOREIGN PATENT DOCUMENTS

| | | |
|---|---|---|
| 1263400 | 11/1989 | Canada . |
| 539631 | 4/1985 | Spain . |

OTHER PUBLICATIONS

Maria Altamura and Enzo Perrotta, An Efficient Synthesis of 2–(Halogenomethyl)penems, J. Org. Chem., 1993, 58, 272–274.

Mar., Advanced Organic Chemistry 4th ed. p. 353, 1992.

*Primary Examiner*—Robert Gerstl
*Attorney, Agent, or Firm*—Ridout & Maybee

[57] ABSTRACT

Nizatidine is prepared by reacting N-[2-[[[2-(hydroxymethyl)-4-thiazolyl]methyl]thio]ethyl]-N'-methyl-2-nitro-1,1-ethenediamine, with an aryl- or tert.alkyl-sulfonyl halide in the presence of a tertiary amine base and a sulfonation catalyst to form the corresponding sulfonate ester, reacting the sulfonate ester so formed with an excess of dimethylamine, and recovering the nizatidine so formed.

14 Claims, No Drawings

NIZATIDINE PREPARATION

FIELD OF THE INVENTION

This invention relates to processes for preparing nizatidine, an important pharmaceutical in the treatment of peptic ulcers, the full chemical name and chemical structure of which are N-[2-[[[2-(dimethylaminomethyl)-4-thiazolyl]methyl]thio]ethyl]-N'-methyl-2-nitro-1,1-ethenediamine:

BACKGROUND OF THE INVENTION AND PRIOR ART

A commercially attractive process for the preparation of nizatidine should yield the product in a highly pure form, or at least in an easily purifiable form. This is particularly advantageous for the last step in a pharmaceutical product synthesis. One general approach to this is the design of a process in which the immediate precursor compound of the final pharmaceutical product differs therefrom, to a significant degree, in respect of acidity or basicity, so that acid/base reactions can be used in separating final product from unreacted precursor.

Nizatidine has Bronsted basicity, i.e. basicity towards protons, derived essentially from the dimethylamino group on the thiazole ring acting in concert with the nitrogen of the thiazole ring. If, therefore, in the final synthetic step of making nizatidine, there is used a precursor which is much more weakly basic than nizatidine, separation of the nizatidine products from the precursor and other by-products can be achieved using simple acid/base reactions and extractions. Such processes are rugged, in the sense that they can be readily scaled up and are relatively insensitive to parameter variables.

U.S. Pat. No. 5,541,335 Manning, issued Jul. 30, 1996, discloses one such process. According to this patent, nizatidine is prepared by reacting N-[2-[[[2-(hydroxymethyl)-4-thiazolyl]methyl]thio]ethyl]-N'-methyl-2-nitro-1,1-ethenediamine, of formula:

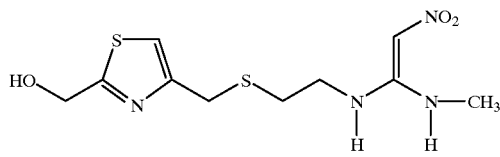

with excess dimethylamine and an (N,N-dimethylamino) phophonium halide such as (N,N-dimethylamino) triphenylphosphonium bromide. The hydroxymethyl reactant has a much lower basicity than the dimethylamino product, nizatidine, thereby allowing ready separation and purification of the product mixture. However, the phosphonium reagents and the solvents proposed for use in this process are complex and costly.

U.S. Pat. No. 5,574 054 Kitagawa et al. (Zeria), issued Nov. 12, 1996 discloses quaternary ammonium salts and nizatidine salts of nizatidine and the like, for use in treating gastrointestinal disorders. In one process for preparing these compounds N-[2-[[[2-(hydroxymethyl)-4-thiazolyl]methyl]thio]ethyl]-N'-methyl-2-nitro-1,1-ethenediamine is first prepared and is then chlorinated with phosphorus oxydichloride to the corresponding 2-chloromethyl compound. Preparation of corresponding acid residue compounds, e.g. by reaction with methanesulfonic acid chloride and toluene sulfonic acid chloride, is also suggested.

SUMMARY OF THE INVENTION

It is an object of the present invention to provide a novel process for the preparation of nizatidine.

It has now been discovered that nizatidine can be prepared in a manner which retains the advantages of the aforementioned Manning process i.e. from the precursor N-[2-[[[2-(hydroxymethyl)-4-thiazolyl]methyl]thio]ethyl]-N'-methyl-2-nitro-1,1-ethenediamine, and using relatively simple and readily available chemical reagents, namely an aryl or tertiary alkyl sulfonyl halide, and relatively cheap and common solvents, provided that certain reaction conditions are observed.

The reaction takes place in two stages. In the first stage, a sulfonate ester is formed, and this first stage requires the presence of a sulfonation catalyst, and the presence of a tertiary amine base to react with the hydrogen halide acid condensation product which is formed. It also uses mild reaction conditions. These combine to ensure that the sulfonate ester is formed rapidly, substantially avoiding attack by the sulfonyl chloride on the secondary amine groups present in the thioether side chain of the precursor, a chemical attack which would ordinarily be expected with such reagents. In the second stage, the sulfonate ester so formed is reacted with an excess of dimethylamine, to form nizatidine.

The process is both simpler and cheaper than that described in the aforementioned Manning patent, and surprising in the context thereof, in its ability to make use of common, relatively cheap reagents and solvents. It appears to be selective in the requirement for use of an arylsulfonyl halide or a tertiary alkylsulfonyl halide in formation of the reactive esterified hydroxyl compound, i.e. the sulfonate ester. Superficially analogous compounds such as methyl sulfonyl chloride do not appear to work satisfactorily, probably due to the presence in such a compound of a hydrogen bound to a carbon atom directly bonded to the sulfonyl group, which when present can lead to degradation of the reagent. Moreover, it is environmentally more acceptable than the process of the Manning patent, in avoiding the use of the potential carcinogens such as hexamethylphorphoramide as reagents.

At the same time, the process of the present invention retains the advantages that the precursor are not strong bases, whereas nizatidine is. Accordingly, nizatidine prepared in this manner is easily separated from the reaction mixture, and purified.

Thus according to the present invention, there is provided a process for preparing nizatidine, N-[2-[[[2-(dimethylaminomethyl)-4-thiazolyl]methyl]thio]ethyl]-N'-methyl-2-nitro-1,1-ethenediamine, which comprises reacting N-[2-[[[2-(hydroxymethyl)-4-thiazolyl]methyl]thio]ethyl]-N'-methyl-2-nitro-1,1-ethenediamine with an aryl- or tert.alkyl-sulfonyl halide in the presence of a tertiary amine base and a sulfonation catalyst to form the corresponding sulfonate ester, reacting the sulfonate ester so formed with an excess of dimethylamine, and recovering the nizatidine so formed.

DESCRIPTION OF THE PREFERRED EMBODIMENTS

The hydroxymethyl starting material, i.e. N-[2-[[[2-(hydroxymethyl)-4-thiazolyl]methyl]thio]ethyl]-N'-methyl-2-nitro-1,1-ethenediamine, can be prepared by processes described in the aforementioned U.S. Manning patent. This involves reaction of 4-[[(2-aminoethyl)thio]methyl]-2-hydroxymethylthiazole with 2-methylamino-2-methylthio-1-nitroethylene.

Mild reaction conditions and low temperatures are preferred for both stages of the reaction, i.e. both the reaction of N-[2-[[[2-(hydroxymethyl)-4-thiazolyl]methyl]thio]ethyl]-N'-methyl-2-nitro-1,1-ethenediamine, with the sulfonyl halide in the presence of tertiary amine base and sulfonation catalyst, and the reaction of the benzenesulfonate ester so formed with excess dimethylamine. The hydroxymethyl starting material, the sulfonate ester intermediate and nizatidine can all over-react with the sulfonyl halide, to give reduced yields and undesirable by-products. This can be minimized by use of mild reaction conditions. Reaction temperatures of room temperature (25° C.) and below are suitable, with temperatures from about 0 to about −35° C. being preferred, along with reaction times of about 1–4 hours, for the combined reaction steps.

Suitable sulfonation catalysts for use in the present invention include 4-(N,N-dimethylamino)-pyridine and 4-(N-pyrrolidinyl)-pyridine. 4-Dimethylaminopyridine is especially preferred. It is most suitably used in amounts from about 2.5–7.5 mole percent, based on the amount of precursor starting material N-[2-[[[2-(hydroxymethyl)-4-thiazolyl]methyl]thio]ethyl]-N'-methyl-2-nitro-1,1-ethenediamine.

Preferred tertiary amine bases for use in the process, for reacting with the hydrogen halide formed in the first stage of the reaction are sterically hindered tertiary amine bases, and especially volatile such bases, so that their residues can be readily separated from the product. Triethylamine is a suitable preferred example.

The preferred arylsulfonyl halides are benzenesulfonyl chloride and toluenesulfonyl chloride, with benzenesulfonyl chloride being most preferred. The preferred tertiary alkylsulfonyl halide is tert.butylsulfonyl chloride. The stoichiometric ratio of starting alcohol to sulfonyl chloride is preferably 0.9:1 to 1.1:1, most preferably 0.95:1 to 1.05:1. The reaction time for the first stage is suitably 2–3 hours. The tertiary amine base, e.g. a tri(lower alkyl) amine such as triethylamine, such be present in the reaction mixture in amounts suitable for it to fulfill its function of reacting with the hydrogen halide condensation product formed in the reaction. Such amounts are generally from about 0.9–2 molar equivalents of amine, based on the amount of N-[2-[[[2-(hydroxymethyl)-4-thiazolyl]methyl]thio]ethyl]-N'-methyl-2-nitro-1,1-ethenediamine, but the amounts are not critical.

The intermediate compound, namely the reactive sulfonyl ester (esterified hydroxyl), does not need to be isolated and purified. It is preferred to react it in situ, without recovery from the initial reaction mixture, by addition thereto of excess dimethylamine. A large excess, e.g. at least 10 equivalents, of dimethylamine is preferably used, with the reaction temperature for the second stage being suitably about the same as that for the first stage. The solvent can be the same in both stages, and is suitably an organic, inert polar solvent appropriate for the relatively low reaction temperatures preferably used, e.g. methylene chloride. An aqueous solution of dimethylamine, as commercially available can conveniently be used. The water from such a solution does not significantly interfere in the reaction. The reaction time for the second stage is suitably of the order of one hour.

The sulfonate ester which is formed as an intermediate in the process of the present invention corresponds to the formula:

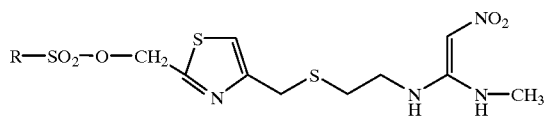

where R represents phenyl or tert.alkyl (preferably $C_1$–$C_4$ tertiary alkyl).

The recovery of the product nizatidine from the reaction mixture is simply accomplished by acidification and solvent extraction of the non-basic materials under acidic conditions, followed by basification and solvent extraction of the nizatidine product under basic conditions. The nizatidine can be purified as an oxalate salt, or by other means known in the art.

The invention is further described for illustrative purposes in the following specific example.

SPECIFIC DESCRIPTION OF THE MOST PREFERRED EMBODIMENT

In a 100 ml three-necked round bottomed flask, filled with a nitrogen atmosphere, equipped with a thermometer, stir bar and dropping funnel and installed in a temperature controlled cooling bath was placed 2.0 g of N-[2-[[[2-(hydroxymethyl)-4-thiazolyl]methyl]thio]ethyl]-N'-methyl-2-nitro-1,1-ethenediamine, prepared according to the process described in U.S. Pat. No. 5,541,335. Into the same flask was added 120 ml of methylene chloride, 2.0 g of triethylamine, and 0.04 g of 4-dimethylaminopyridine. The contents were cooled to −20° C. internal. To this mixture was added dropwise from the pressure-equalized dropping funnel 1.3 g of benzenesulfonyl chloride in 18.0 ml of methylene chloride so as to maintain the internal temperature of the reaction mixture at or below −20° C. When the starting material was almost entirely consumed (2–3.5 hours), as determined by thin layer chromatography on silica gel eluting with 8/2 v/v EtOAc/MeOH, approximately 7.0 ml of dimethylamine was condensed into the reaction mixture. The temperature was held at or near −20° C. When the intermediate had disappeared, as indicated by TLC, the volatile components of the mixture were removed under vacuum and the residue dissolved in 15 ml methylene chloride and 8.0 ml water. The pH of the aqueous phase was adjusted to pH 4.5 by addition of 3N HCl. This acidification aids dissolution. The lower organic layer was separated and the aqueous phase was washed twice with 8.0 ml portions of methylene chloride. The aqueous phase containing the product was retained and adjusted to pH 10.5 using saturated potassium carbonate solution. The separated crude product was extracted with three 15 ml portions of methylene chloride, which were combined and evaporated. To remove trace amounts of methylene chloride, the product was twice evaporated to dryness from a slurry in isopropanol. The residue was then dissolved hot in 20.0 ml of isopropanol and allowed to crystallize. The solid was cooled to 0–5° C. for 16 hours and then filtered and washed with cold isopropanol. The solid was dried at 40° C. under vacuum, to give 1.1 g (50.3%) of nizatidine.

What is claimed is:

1. A process for preparing nizatidine, N-[2-[[[2-(dimethylaminomethyl)-4-thiazolyl]methyl]thio]ethyl]-N'-methyl-2-nitro-1,1-ethenediamine, which comprises reacting N-[2-[[[2-(hydroxymethyl)-4-thiazolyl]methyl]thio]ethyl]-N'-methyl-2-nitro-1,1-ethenediamine with an aryl- or tert.alkyl-sulfonyl halide in the presence of a tertiary amine base and a sulfonation catalyst to form the corresponding sulfonate ester, reacting the sulfonate ester so formed with an excess of dimethylamine, and recovering the nizatidine so formed.

2. A process according to claim 1 wherein the tertiary amine base is a volatile, sterically hindered tertiary amine.

3. A process according to claim 2 wherein the tertiary amine base is triethylamine.

4. A process according to claim 2 wherein the sulfonation catalyst is selected from 4-dimethylaminopyridine and 4-pyrrolidinopyridine.

5. A process according to claim 1 wherein the sulfonation catalyst is 4-dimethylaminopyridine.

6. A process according to claim 1 wherein the sulfonyl halide is benzenesulfonyl chloride.

7. A process according to claim 1 wherein the reaction of the sulfonate ester so formed with dimethylamine takes place in situ.

8. A process according to claim 7 wherein the reaction temperature is from about 0° C. to −35° C.

9. A process according to claim 8 wherein the molar ratio of N-[2-[[[2-(hydroxymethyl)-4-thiazolyl]methyl]thio]ethyl]-N'-methyl-2-nitro-1,1-ethenediamine to aryl- or tert.alkyl-sulfonyl chloride is from about 0.9 to 1.1.

10. A process according to claim 9 wherein the sulfonation catalyst in the first stage reaction is used in an amount of from about 2.5–7.5 mole percent.

11. A process according to claim 10 wherein the molar ratio of N-[2-[[[2-(hydroxymethyl)-4-thiazolyl]methyl]thio]ethyl]-N'-methyl-2-nitro-1,1-ethenediamine to aryl- or tert.alkyl-sulfonyl chloride is from about 0.95 to 1.05.

12. A process according to claim 1 wherein N-[2-[[[2-(hydroxymethyl)-4-thiazolyl]methyl]thio]ethyl]-N'-methyl-2-nitro-1,1-ethenediamine is reacted in a first stage with benzenesulfonyl chloride at a relative molar ratio of from about 0.96–1.05, at a temperature of from 0 to −30° C., in the presence of 4-dimethylaminopyridine as sulfonation catalyst in an amount from about 2.5–7.5 mole per cent and in the presence of triethylamine as tertiary amine base, and in a second stage the sulfonate ester so formed is reacted in situ with dimethylamine at a temperature of from 0 to −30° C.

13. 2-Sulfonate-esters of [[4-thiazolyl]methyl]-thioethyl-N'-methyl-2-nitro-1,1-ethenediamine of general formula:

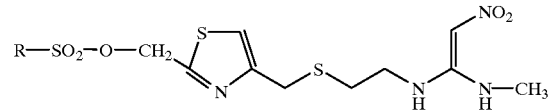

in which R represents phenyl or tert.butyl.

14. 2-Sulfonate esters according to claim 13 in which R represents phenyl.

* * * * *